United States Patent [19]
Hickner et al.

[11] 4,126,746
[45] Nov. 21, 1978

[54] HALOHYDRIN THIOETHERS AND METHOD OF PREPARATION

[75] Inventors: Richard A. Hickner; Corwin J. Bredeweg, both of Midland, Mich.

[73] Assignee: The Dow Chemical Company, Midland, Mich.

[21] Appl. No.: 170,297

[22] Filed: Aug. 9, 1971

Related U.S. Application Data

[62] Division of Ser. No. 764,956, Oct. 3, 1968, abandoned.

[51] Int. Cl.² .............................................. C07D 251/30
[52] U.S. Cl. ................................. 544/219; 260/609 R; 260/347.2; 260/326.84; 260/558 S; 260/559 T; 260/561 S; 260/562 S; 260/557 R; 260/401
[58] Field of Search .................... 260/248 CS, 248; 544/219

[56] References Cited

U.S. PATENT DOCUMENTS

| 3,214,325 | 10/1965 | Gaertner | 260/248 X |
| 3,293,249 | 12/1966 | Biland et al. | 260/248 |
| 3,644,410 | 2/1972 | Gregg et al. | 260/248 |

Primary Examiner—John M. Ford
Attorney, Agent, or Firm—Glwynn R. Baker

[57] ABSTRACT

Compounds of the structure $R(SCH_2CHOHCH_2X)_n$ when $n = 1$ to 4 and R is a hydrocarbon, ether, ester, acetal, hydroxy aliphatic, hydroxy aromatic, imide or amide group or halogenated derivatives thereof are prepared by reacting 1-halo-3-mercapto-2-propanol with an aliphatically unsaturated compound using free radical initiators as catalysts. The compounds in which R is an unsaturated aliphatic hydrocarbon group of 2 to 24 carbon atoms, or an unsaturated cycloaliphatic group, and those in which the aliphatic or cycloaliphatic group is connected to two or more $-S-CH_2-CHOHCHCl$ groups, and compounds where R is an alkylene substituted aromatic group and hydroxy, thioalkyl, alkoxy, aryloxy, ester, carbamidoalkyl and sulfamidoalkyl, halogenated derivatives of said groups are new compounds. The thioether halohydrins can be converted to epoxides. The process utilizing a radioactive energy source as a catalyst is new.

2 Claims, No Drawings

HALOHYDRIN THIOETHERS AND METHOD OF PREPARATION

This application is a division of our prior application Ser. No. 764,956, filed Oct. 3, 1968 for New Halohydrin Thioethers and Method of Preparation now abandoned.

Summary of the Invention

This invention relates to novel thioethers having vicinal —OH and halogne groups and to methods of manufacture of halohydrin thioethers by reacting a halohydroxy thiol with a compound having alicyclic or aliphatic carbon-to-carbon unsaturation. More particularly, the invention pertains to methods of making thioethers of the structure R—(—S—CH$_2$CHOHCHX)$_n$, where R is a hydrocarbon, ether, ester, acetal, alcohol, imide or amide group or a halogenated derivative thereof, $n$ is an integer of 1 to 4 inclusive and X is chlorine or bromine, and to certain novel compounds of the above generic structure. The thiocthere are prepared by reacting 1-halo-3-mercaptopropanol-2 with a compound having aliphatic carbon to carbon unsaturation in the presence of a free radical initiating catalyst. The reaction is effective with monoolefinic compounds, which form derivatives with a single —S—CH$_2$CHOHCH$_2$X group and polyolefinic compounds, to form derivatives with a plurality of —SCH$_2$CHOHCH$_2$X groups and with acetylenic compounds where one to two —SCH$_2$CHOHCH$_2$X groups are added to each acetylenically unsaturated group.

Each new compound has at least three reactive sites in that the halogen is labilo and can be hydrolyzed under proper conditions to form the corresponding glycol, each can be esterified with carboxylic acid anhydrides to convert the OH to an ester group or each can be dehydrohalogenated to form an epoxide. The epoxides can be polymerized by known procedures to form homopolymers from single compounds and copolymers from mixtures of epoxides. The epoxides are stabilizers for vinylidine chloride homopolymers and copolymers of vinyl and vinylidene chlorides with other monoolefinically unsaturated monomers. For stabilizing the vinyl and vinylidene chloride-containing homopolymers or copolymers, concentrations of 1 to about 5% by weight of the epoxide based on the weight of the polymers is usually sufficient. The epoxides are also useful for treating textiles having active H atoms, such as cellulose, to provide improved crease resistance.

The prior art processes for preparing halohydrin thioethers used Lewis acids, such as zinc chloride, to catalyze the reaction between an epihalohydrin and a mercaptan. These catalysts also effect polymerization of the epihalohydrins, which resulted in poor yields of desired derivatives and made separation of desired compounds quite difficult. Other processes known to the art all require a mercaptan as a starting material. Many of the mercaptans are not readily accessible.

It has now been found that a wide variety of new and useful halohydrin thioethers can be prepared simply and in good yields, without undue by-product formation. Another advantage is that one small class of halomercaptopropanols can be reacted with a very wide variety of readily available alicyclically or aliphatically unsaturated compounds to form halohydrin thioethers.

Another advantage is that it is possible to form compounds having a multiplicity of —SCH$_2$CHOHCH$_2$X side groups.

A further advantage is that when radiation catalysis is employed, no extraneous ingredients are added to the reaction mixture.

The sulfur atom of the RSCH$_2$CHOHCH$_2$X compounds is always attached to an aliphatic group of at least 2 C atoms, or to a saturated cycloaliphatic ring. Thus, R in the generic structure represents an aliphatic hydrocarbon group of from 2 to 18 C atoms, an alkoxyalkyl, a polyoxypolyalkenyl, alkylcarboxy, alkylcarboxyethyl, an alkenyl, an alkylcarbamidoalkyl, a hydroxyalkyl, an aralkyl, aralkoxy, aroxyalkyl, arylcarboxyalkyl, arylcarbamidoalkyl, alkylcarbimidoalkyl, hydroxyaralkyl, hydroxyaroxyalkyl, cyclohexyl, cycloctenyl, cyclohexylalkyl and bridged polynuclear terpene residue, halogen substituted derivatives of said groups and a tetrahydrofurfuryl or pyrrolidinyl nucleus.

Compounds in which R is alkenyl, haloalkyl, haloalkenyl, alkylcarboxy, alkoxyalkyl, polyoxypolyalkenyl, alkylcarboxyalkyl, alkylcarbamidoalkyl, alkylcarbimidoalkyl, and all the aromatic ring containing groups represent new compounds of this invention.

Both olefinic and acetylenic groups react with the 1-halo-3-mercapto-2-propanols to form monoadducts with monoolefins, mono and diadducts with acetylenic linkage and mono and polyadducts with polyolefinically unsaturated compounds.

Although the invention is exemplified by reactions of relatively pure compounds, it is to be understood that mixtures of olefinically and/or acetylenically unsaturated compounds can be reacted with the halomercaptopropanol to form a mixture of adducts.

The reaction can be effected at any temperature where the individual reactants are liquid. In cases where one reactant is gaseous at room temperature, the reaction can be carried out under sufficient pressure to liquify the gaseous ingredient or at a temperature low enough to liquify the gas. In certain instances, it may be most desirable to carry out the reaction in a common solvent which is nonreactive with either the unsaturated compound or the halomercaptopropanol and which has a low freezing temperature. A common solvent of the above-described type may also be desirable with some unsaturated compounds which are solid at reaction temperature. Typical solvents are the lower alkanols of from 1 to about 6 C atoms, liquid alkanes and hydrocarbons having only aromatic unsaturation and halogenated derivatives of such hydrocarbons.

The reaction can be carried out at temperatures ranging from about −50° C. to about 150° C. The reaction rate, however, is usually sufficiently satisfactory at 25° to 80° C. and therefore this range is preferred.

The free radical initiators that can be employed include azo compounds, examples of which are azobisisobutyronitrile and azobisisobutyric acid, carboxylic acid peroxides such as benzoyl peroxide, ring halogenated derivatives thereof, caprylyl peroxide, other organic peroxides such as ditertiary butyl peroxide t-butylhydroperoxide, ultraviolet light and ionizing radiation. The preferred free radical initiators are ultraviolet light and ionizing radiation given off by radioactive isotopes, and combinations of ultraviolet light and ionizing radiation, for the reason that they induce little polymerization and do not add any extraneous materials which may have an effect on subsequent separation of ingredients.

The reaction between the unsaturated compounds and the 1-halo-3-mercapto-2-propanol can be shown generically as $$R(-CH_2=CH_2)_n + X-CH_2-CHOHCH_2SH \xrightarrow[\text{radical initiator}]{\text{free}} R-(CH_2-CH_2SCH_2CHOHCH_2X)_n$$

where R, X and n are the same as defined above. It is to be understood that the olefinic group of the reactant need not be terminal, although the latter are considerably more reactive, in general, than internal olefinic groups.

The examples which follow are intended to illustrate the invention, but not limit it. All parts are by weight unless otherwise specifically indicated.

DETAILS OF DISCLOSURE

Hydrocarbon Derivatives Aliphatic

EXAMPLE 1

A 600 ml. beaker fitted with a magnetic stirrer and immersed in a water bath through which cooling water was circulated, was charged with 0.5 mole of 1-chloro-3-mercapto-2-propanol and 0.5 mole of octene-1 was added dropwise. The beaker was irradiated with an UA-2 ultraviolet ray lamp. The temperature was maintained at about 20°–30° for 1 hour. At the beginning of the reaction period, two immiscible layers were apparent. However, after about 1–5% of the olefin reacted with the 1-chloro-3-mercapto-2-propanol, the mixture became completely miscible.

The mixture was then separated by distillation. The fraction boiling at 118°–119° C. at 0.1 mm. Hg. was found to be $C_8H_{17}-S-CH_2-CH_2OHCH_2Cl$. It had a refractive index at 25° C of 1.4828. On analysis it was found to contain 56.48% C, 10.08% H and 13.69% Cl. The yield based on he olefin was substantially quantitative.

EXAMPLES 2–4

The procedure disclosed in Example 1 was followed with decene-1, hexene-2, and pentene-2 as representative monoolefins which can be reacted to form a derivative having the formula $R-S-CH_2CHOHCH_2Cl$, where R represents the hydrocarbon group derived from the olefin. Tabulated below are the reaction conditions and results obtained.

TABLE I

| Ex. | Olefin | Moles CMP/Olefin | Hrs. U.V. Exposure | Percent Yield | B.P. Deg. C. /0.2 mm. | n 25° D |
|---|---|---|---|---|---|---|
| 2 | $C_{10}H_{20}$ | 1.25 1 | 1.75 | 91 | 137–7 | 1.4840 |
| 3 | $C_6H_{12}$ | 1.25 1 | 7 | 80 | 82–6 | 1.4901 |
| 4 | $C_5H_{10}$ | 1.5 1 | 1.67 | 79 | 172–3 | 1.4932 |

CMP = 1-Chloro-mercapto-2-propanol.

These data show that good yields of the adduct can be obtained with olefins having terminal or non-terminal unsaturation. With some olefins having non-terminal unsaturation, it is necessary to carry on the reaction for a longer time than with terminal olefins. However, pentene-2 reacted about as fast as a terminal olefin.

The alkene which can be reacted with the chloromercaptopropanol can contain from 2 to about 24 carbon atoms.

With alkadienes, usually a mixture of mono- and diadduct is formed, although the diadduct can be formed to the substantial exclusion of monoadduct if an excess of halomercaptopropanol is employed for fairly long reaction periods. Best yields of mono-adduct are obtained by using an excess of diolefin and slow addition of the 1-chloro-3-mercapto-propanol-2 to the diolefin. In some instances, it is desirable to employ a common inert solvent for the diene and chloromercapto propanol to assure that a single phase is present during the entire reaction period.

EXAMPLE 5

An 800-ml. beaker cooled with external cooling coils was charged with 1.5 moles of 1,5-hexadiene and 35 g. of isopropyl alcohol. The mixture was stirred with a magnetic stirrer and irradiated with a UA-2 ultraviolet lamp while adding 1.5 moles of 1-chloro-3-mercapto-2-propanol over a period of 3.75 hours. The mixture was thereafter irradiated for 3.5 additional hours, using a $Co^{60}$ source. The mono-adduct $(CH_2=CH(CH_2)_4-S-CH_2CH_2OHCH_2Cl)$ was flash distilled from the mixture at a temperature of about 90°–105° C at 0.1 mm. and then redistilled through a fractionating column at 95°–97° C and .1 mm. pressure. The colorless liquid weighed 69 g. The residue from the flash distillation was diadduct. When this reaction was repeated with a ratio of 4 moles of the chloromercaptopropane with 1 mole of the diene and a reaction time of 7 hours, a 74% conversion of the diene to the diadduct, which had the structure $ClCH_2CHOHCH_2S-(CH_2)_6SCH_2CHOHCH_2Cl$, was obtained.

EXAMPLE 6

The procedure of Example 5 was repeated using 1 mole of 1,7-octadiene and 1 mole of 1-chloro-3-mercapto-2-propanol. The monoadduct after flash distillation and redistillation through a fractionating column weighed 70.2 g.

Repeating this run with 2 moles of the chloromercaptopropanol with one mole of 1,7-octadiene and a reaction time of three hours resulted in a 97% yield and 84% conversion of the diene to the diadduct.

EXAMPLE 7

A mixture of 1-chloro-3-mercapto-2-propanol and butadiene in a molar ratio of 2 to 1 was exposed to ultraviolet light for ¾ hour at a temperature of −5° to −20° C. The yield of 1,4 monoadduct was 35%. It had a B.P. at 0.2 mm. of 71–73 and a refractive index of 1.5169.

In order to obtain best yields with gaseous olefins, it is preferred to add the olefin to the chloromercaptopropanol under sufficient pressure to maintain the olefin in a liquid state at a temperature of about 10°–30° C.

The monoadducts of the dienes can be used as comonomers with alkadienes or polymerizable monoolefinic compounds to provide copolymes having very reactive side chains.

Alkenecyclohexenes

EXAMPLE 8

A mixture of 21.6 g. of 4-vinyl cyclohexene (0.2 mole) and 25.2 grams (0.2 mole) of 1-chloro-3-mercapto-2-propanol in an externally cooled beaker to maintain the temperature at 20°–25° C, was irradiated for 5.5 hours with a UA-2 ultraviolet lamp. Stirring was continued during the irradiation period. Flash distillation of the reacted mixture yielded 24.3 g. of monoadduct boiling at 132°–144° C at 0.1 to .15 mm. pressure. The refractive index was 1.5302. Analysis of the monoadduct fraction by nuclear magnetic resonance indicated that the product was about a 3 to 1 mixture of

-CH₂CH₂SCH₂CH₂OHCH₂Cl and

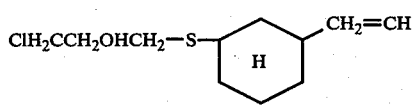

Analysis of the mixture showed that it contained 56.5% C and 15.28% Cl. The calculated values for the monoadduct are C 56.27% and Cl 15.10%.

The residue in the distillation vessel weighed 13.5 g. It was the diadduct

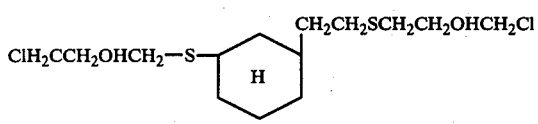

The reaction of 4-vinyl cyclohexene appears to begin immediately upon commingling the ingredients, so that catalysis is not essential if some additional time is allowed for the reaction to proceed.

In one run where a molar ratio of 3 chloromercaptopropanol per one of diene was used without a catalyst for 24 hours, a mixture resulted which contained 53% of the monoadduct and 47% of the diadduct.

The reaction of 1,2,4-trivinylcyclohexane with the chloromercaptopropanol in a molar ratio of 1 to 2, respectively, produces a mixture of the triadduct, monoadduct, and isomeric diadducts.

In another example, 202 g. (1.6 moles) of 1-mercapto-3-chloro-2-propanol was charged to a 500 ml. three neck flask fitted with stirrer, condenser, nitrogen sparge and dropping funnel. A solution of 1.31 g. (0.008 mole) of azobisisobutyronitrile in 65 g. (0.4 mole) of 1,2,4-trivinylcyclohexane was added to the mercaptan at 70° during three hours. After heating for two hours longer, an additional 1.31 g. of catalyst was added, and heating continued for an additional seven hours. The crude product was charged to a flash still and 81 g. of unreacted mercaptan removed by heating to 120° at 0.5 mm. The net weight of the product was 180 g. corresponding to 0.91 mole of mercaptan reacted or an average of 2.3 double bonds reacted.

Cycloalkenes

EXAMPLE 9

A mixture of a 2:1 molar ratio of chloromercaptopropanol to cyclopentadiene was exposed to ultraviolet light for two hours at room temperature. About 26% of the diene reacted to form the monoadduct and 14% formed the diadduct.

EXAMPLE 10

The reaction of 1-chloro-3-mercapto-2-propanol with dicyclopentadiene in a molar ratio of 2.2 to 1, respectively, for 2½ hours at approximately room temperature with UV irradiation resulted in complete conversion of the olefin. About 58% was the diadduct and 42% was monoadduct. The monoadduct boiled at 137°-144° at 0.1 mm., n 25/D 1.5556 while the diadduct remained as a pot residue.

EXAMPLE 11

A mixture of 1,5-cyclooctadiene and 1-chloro-3-mercapto-2-propanol in a molar ratio of 1 to 2.4, respectively, was exposed to ultraviolet radiation for 5 hours at approximately room temperature. It was found that about 92% of the diene was reacted and the conversion to the monoadduct was 65%. The exact structure of the diadduct formed was not determined, since two positional isomers each could exist as cis-trans pairs.

By substituting 1,3-cyclooctadiene for the 1,5 isomer and using an irradiation period of 14½ hours, a 91% yield with a 76% conversion to monoadduct was obtained. The 1,2- and 1,4-monoadducts were obtained as well as a diadduct of unidentified structure.

The monoadducts of the cyclic dienes can be employed in the same manner as the monoadducts of the alkadienes.

Terpene and Bicycloalkene Derivatives

EXAMPLE 12

Terpene hydrocarbons and bicycloalkenes also react with 1-chloro-3-mercapto-2-propanol to form adducts. Tabulated below are results obtained with certain representative bicycloalkenes or terpene compounds. In all cases, the runs were made at about room temperature.

TABLE II

| Terpenes | Mols CMP/ Mol Terp. | U.V. Exposure Hrs. | % / Yield | % Monoadd. | % Di %-add. |
| --- | --- | --- | --- | --- | --- |
| 5-methylene-2-norbornylene | 2:1 | 1 | 99 | 32 | 67 |
| Endo dicyclopentadiene | 4:1 |  | 100 | 91 | 9 |
| Dipentene | 4:1 | 7 | 80 | 0 | 80 |
| 2,2,1-bicycloheptadiene | 1:1 | ½ | 98 | 20 | 80 |

The monoadduct from 5-methylene-2-norbornylene may be either unsaturated or a saturated nortricyclene derivative. The unsaturated product is a mixture of the structure

CH₂SCH₂CHOHCH₂Cl and

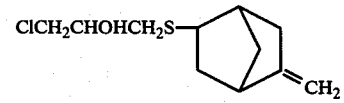

while the nortricyclene structure is probably

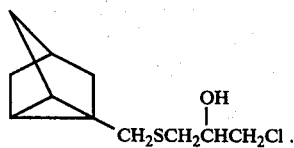

In place of the naturally occurring dl-dipentene, one may also use the pure d-isomer, d-limonene. Either of these substances can form a monoadduct of the structure

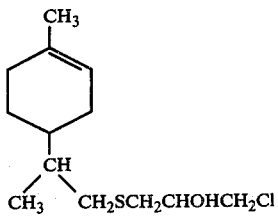

2,2,1-Bicycloheptadiene is capable of forming two monoadducts. The structure of these is shown by nuclear magnetic spectroscopy to be a mixture of

The latter isomer is favored by a low mercaptan to olefin ratio while the former isomer is favored by a high mercaptan to olefin ratio. Since at high mercaptan to olefin ratios diadduct may be formed, to obtain maximum yields of the unsaturated monoadduct, the reaction must be stopped at low conversion.

Other terpenes reacted with obtainment of good yields of adduct:

| Terpene | Product Formed |
| --- | --- |
| Alpha pinene | CH$_3$ |
| Beta pinene | S—CH$_2$CHOHCH$_2$Cl |
|  | CH$_2$SCH$_2$CHOHCH$_2$Cl |
| Δ$^3$ Carene | ClCH$_2$CHOHCH$_2$S— (with CH$_3$, CH$_3$) |

Other terpenes which can be reacted include camphene, subinene, d-fenchene, β-fenchene, and β-phellandrene.

Aromatic Substituted Olefins

EXAMPLE 13

Typical aromatic substituted monoolefins used to exemplify the invention are styrene, alpha methyl styrene and p-ethyl styrene. It is understood that the aromatic portion of the molecule can contain any other substituents which are non-reactive with the halomercapto propanol. Representative substituents are halogen, alkyl, carboxy, ester, sulfone, cyano, nitro and tertiary amino groups. The aromatic group can be mono or polycyclic and the latter can be fused or non-fused.

The procedure employed for reacting alpha-methylstyrene was to permit the mixture of reactants to stand for two weeks at room temperature before work-up. All other mixtures were exposed to ultraviolet light for short periods of time.

TABLE III

| Olefin | Mole Ratio CMP/olefin | Hrs UV Exp. | % Yield | B.P.° C per mm. | N 25° D |
| --- | --- | --- | --- | --- | --- |
| Styrene | 2:1 | 3-¼ | 85 | 140/0.1 | 1.5640 |
| α-Me. Styrene | 2:1 |  | 65 | 132-6/0.1 | 1.5571 |

Halogenated hydrocarbons can be readily reacted by the same procedure as that described above. Representative reactants are vinyl chloride, allyl chloride, the butenyl chlorides, allyl fluoride, 1,1,2-trifluoro-2-chloro-ethylene, 1,1,2-trifuoroethylene, 3,3,3-trifluoro-1-propene and p-chlorostyrene.

In the examples below, the procedure followed was that described in Example 1. The conversion of mercaptan to adduct with vinyl chloride was 25%. The derivative had the structure ClCH$_2$CH$_2$S—CH$_2$CHOHCH$_2$Cl.

When highly polymerizable olefins such as styrene, p-chlorostyrene, or vinyl chloride are utilized, the product will consist of telomers in addition to the 1:1 adduct. These telomers have the general formula

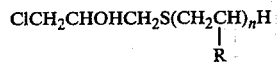

where R is phenyl, chloro, or cyano and n is an integer up to about five. Formation of 1:1 adduct is favored by high mercaptan to olefin ratios, while telomerization is favored by low mercaptan to olefin ratios.

EXAMPLE 14

Polyolefinically substituted aromatic compounds can be also reacted to form derivatives in which part or all of the olefinic substituents are saturated. Thus, if it is desired to retain any degree of unsaturation in the adduct, the amount of halomercapto propanol added is adjusted to less than the stoichiometric amount needed to saturate the olefinic substituents on the aromatic rings. If saturation of the olefinic bonds is desired, it is preferred to employ an appreciable excess over that stoichiometrically required, because the addition reaction does not always go to completion with merely molar equivalents of olefinic unsaturation and the halomercapto alcohol.

In general, the polyadducts are high boiling materials which are difficult to distill. However, flash distillation is effective for removing any unreacted halo-mercapto propanol and in many instances, the monoadduct.

If unsaturation remains on the aromatic compound, typical examples of which are allyl or isopropenyl groups, the adduct can be homopolymerized or copolymerized with other unsaturated compounds by known techniques. Alternatively, the halohydrin group of the adduct can be converted to an epoxide. The epoxide can be homo- or copolymerized. Homopolymers and copolymers obtained from the adducts have reactive OH and halogen groups in the side chains which can be used for crosslinking purposes and for the formation of derivatives.

Listed below are representative polyolefinically-substituted aromatic compounds which can be reacted to form adducts with 1-mercapto-3-halo-2-propanol. In the first four runs, Co⁶⁰ was the irradiation source, and in Run 5, an ultraviolet light source was employed as the catalyst. The first run was exposed to 5 megarads of Co⁶⁰ radiation and Runs 2-4 each was subjected to 3 megarads. The mixtures which were exposed to Co⁶⁰ were placed in a citrate bottle, the air was replaced with nitrogen and the bottles were capped before irradiation. Run 5 was run at room temperature in a beaker.

TABLE IV

| Run No. | Olefin | Mol Ratio CMP/Olefin |
|---|---|---|
| 1 | 1-allyloxy-2-methoxy-4-allylbenzene | 2:1 |
| 2 | 12-diallyloxybenzene | 2:1 |
| 3 | 1-allyloxy-2-allyl-benzene | 2:1 |
| 4 | Diallylether of bisphenol-A | 2:1 |
| 5 | 2,2-bis(3-allyl-4-allyloxy phenyl)propano | 2:1 |

CMP = 1-chloro-3-mercapto-2-propanol

Yields of the above adducts are generally above 80%. In Run 5, only two equivalents of mercaptan were used for four equivalents of unsaturation, so the product will contain, on an average, two sites of unsaturation.

When p-divinyl benzene was added to a 2 mol ratio quantity of chloromercaptopropanol over a period of 20 minutes and irradiated for 5 hours with ultraviolet light, a mixture of compounds was obtained, including one or more telomers having more than 1 divinyl benzene unit for each two chlorohydrin groups. The actual structure of the telomers was not determined. The data showed that about 85% of the chloromercaptopropanol reacted. In two additional runs 132 g. of the divinyl benzene were reacted, respectively, with 126.5 g. and 190 g. of chloromercaptopropanol. In each case the conversion of olefin was complete. In the former case the chloromercaptopropanol was all converted, while in the latter case only a small amount was unreacted.

Diisopropenyl benzene reacts with chloromercaptopropanol in a manner similar to divinyl benzene. The example 0.3 mole of m-diisopropenyl benzene was reacted with 0.6 mole of the chloromercaptopropanol the reaction was carried out in 100 ml. propanol at a temperature of 60° C for 50 hours without catalyst.

Other polyolefinically unsaturated aromatic compounds which readily undergo addition of halomercapto propanol are:

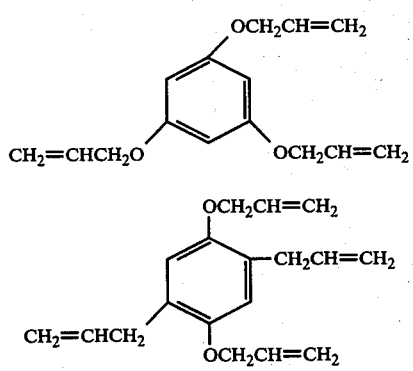

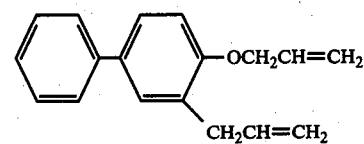

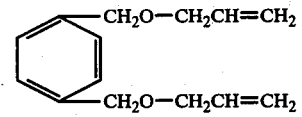

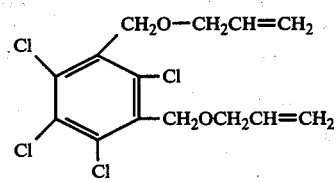

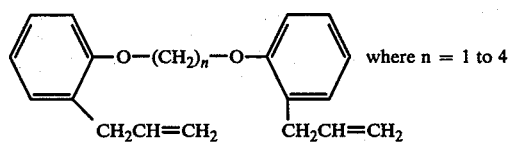

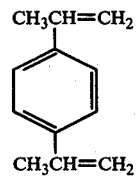

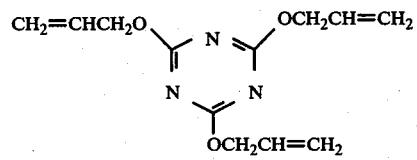

Any compound having the structure $(CH_2=CHCH_2)_nAr(OCH_2CH=CH_2)_x$ when $n = 0 - 2$ and $x = 1 - 3$ and Ar is aromatic, haloaromatic or aralkyl can be used.

Unsaturated Aliphatic Alcohol and Ether Derivatives

EXAMPLE 15

This example shows that alcohols and etheralcohols having aliphatic unsaturation can be reacted with 1-mercapto-3-halo-2-propanol to form adducts having thioether and halohydrin groups.

The unsaturated alcohols can have more than one OH group and can be mono- or polyunsaturated. Acetylenic and olefinic alcohols can be reacted to form adducts. Acetylenic compounds can add two moles of the mercapto halopropanol. Alcohols having from 3-16 carbon atoms can be reacted, but the preferred carbon length of the alcohols is from 3 to 12.

Run 1:

To one mole of 1-mercapto-3-chloro-2-propanol 1 mole of allyl alcohol was added over a period of about an hour. The mixture was stirred and exposed to ultraviolet light during this time. Irradiation and stirring was continued for an additional 10 hours. The crude product was charged to a flash still and unreacted ingredients were removed at 125° C and .2 mm. pressure. The residue contained 18.9% Cl and 18.7% S. It had the structure ClCH$_2$CHOHCH$_2$S(CH$_2$)$_2$CH$_2$OH.

Run 2:

A solution containing 0.25 mol 1-hexene-3-ol and 0.25 mol of 1-mercapto-3-chloro-2-propanol in 100 ml. isopropanol was subjected to 3.6 megarads of radiation from a Co$^{60}$ source. Thereafter the solution was transferred to a beaker and subjected to ultraviolet light for 8 hours. Analysis of the solution by vapor phase chromatography showed that essentially all the reactants were converted.

The sulfur was found to be attached to the terminal carbon atom. The adduct had the structure CH$_3$(CH$_2$)$_2$CHOH(CH$_2$)$_2$SCH$_2$CHOHCH$_2$Cl.

Run 3:

In this run 4-hexene-3-ol was substituted for the terminally unsaturated hexenol of Run 2. Otherwise, the procedure was identical to that described in Run 2. After completion of the irradiation, the mixture was heated to 100° C at 0.3 mm. to remove the solvent and unreacted ingredients. It was found by nuclear magnetic resonance spectroscopy to consist of a mixture of

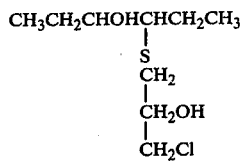

and,

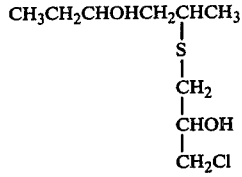

Run 4:

An equimolar mixture of 2-allyl-2-ethyl-1,3-propanediol and 1-mercapto-3-chloro-2-propanol in 50 ml. isopropanol was subjected to irradiation by the procedure described in Run 2. The reacted mixture was flash distilled at 130° C and .2 mm. pressure to remove the solvent and small amounts of unreacted ingredients. Its structure was C$_2$H$_5$C(CH$_2$OH)$_2$(CH$_2$)$_3$SCH$_2$CHOHCH$_2$Cl.

Run 5:

In this run, equimolar quantities of undecenyl alcohol and 1-mercapto-3-chloro-2-propanol were irradiated with Co$^{60}$ until the total dose was 2.0 megarads. The product obtained was a white waxy solid. It had the structure ClCH$_2$CHOHCH$_2$S—(CH$_2$)$_{10}$CH$_2$OH.

Run 6:

A citrate bottle was charged with 0.2 mole of propargyl alcohol and 0.4 mole of 1-mercapto-3-chloro-2-propanol, flushed with nitrogen and sealed. It was exposed to 3 megarads of radiation from a Co$^{60}$ source. The crude product was dissolved in chloroform and extracted with 1.5 N NH$_4$OH to remove small amounts of unreacted mercaptan. The solution was then washed with four portions of water, dried and the CHCl$_3$ was evaporated. The product contained 34.2% C, 24.6% Cl and 22.4% S. The molecular weight by boiling point elevation was 291 as compared to a calculated molecular weight of 308 for the diadduct. The product was a mixture of

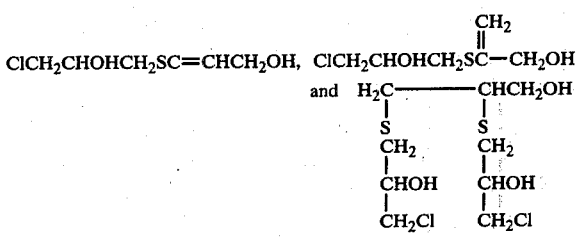

with the latter predominating.

Other representative unsaturated alcohols which react with chloromercaptopropanol are 3,5-dihydroxy-1-pentene, 3-hydroxy-1-heptene, 1,4-dihydroxy-2-butyne. The latter can add 1 or 2 moles of the chloromercaptopropanol to form compounds with the structure

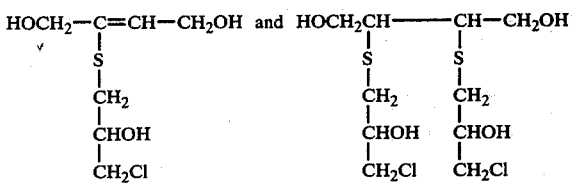

Unsaturated Ether Alcohols

Runs 7-11:

In all these runs unsaturated ether alcohols were reacted with 1-mercapto-3-chloro-2-propanol. Runs 7-9, inclusive, were irradiated with 3.4 megarads from a Co$^{60}$ source. The reactants were dissolved in 100 ml. isopropanol and placed in a citrate bottle before exposure to the radiation. Runs 10 and 11 were made in a beaker using ultraviolet light for 12 and 6 hours, respectively. Run 10 was made without added solvent, and Run 11 was made with 75 ml. of isopropanol. Tabulated below are the unsaturated ether alcohols used and the results obtained.

TABLE V

| Run No. | Ether Alcohol | Molar RAtio of Alcohol to CMP |
|---|---|---|
| 7 | 1-allyloxy-2,2-bis(hydroxymethyl)butane | 1:1 |
| 8 | 1,3-bis(allyloxy)-2,2-di(hydroxymethyl)propane | 1.2:1 |
| 9 | 2,2-bis(allyloxymethyl)-1-butanol | 1:2 |
| 10 | 1-allyloxy-3-chloro-2-propanol | 1:1 |
| 11 | 1-allyloxy-2-(1-chloro-2-hydroxypropoxy)propane | 1:1 |
| 12 | 1-allyloxy-2,2-bis(hydroxymethyl)propane | 1:1 |
| 13 | 1,3-bis(allyloxy)-2-hydroxymethyl-2-ethyl propane | 2:1 |
| 14 | 2-allyloxy ethanol-1 | 1:1 |
| 15 | 2-vinyloxy ethanol-1 | 1:1 |
| 16 | monoallyl ethers of poly(ethylene glycols) having about 10 and 12 (CH$_2$CH$_2$O) units in the chain. | 1:1 |
| 17 | monoallyl ethers of copolymers of ethylene and propylene oxides | |

TABLE V-continued

| Run No. | Ether Alcohol | Molar Ratio of Alcohol to CMP |
|---|---|---|
| | having molecular weights of about 200 to 1000. | 1:1 |
| 18 | Allylglycidyl ether/propylene oxide copolymer (double bond equivalent weight about 353) in isopropanol solution | 1.5:1 |

The yields of adducts in the above examples were generally nearly quantitative.

EXAMPLE 16

Mono- and polyunsaturated ethers and thioethers can be reacted with 1-mercapto-3-halo-2-propanol to form adducts with polyunsaturated ethers, polyadducts or mixtures of mono- and polyadducts can be formed. The ethers can be open-chain or cyclic.

Run 1:

A citrate bottle containing .22 mole of 1,2-di-(allyloxy) ethane and 0.4 mole of 1-mercapto-3-chloropropanol-2 dissolved in 100 ml. isopropanol was subjected to 3.4 megarads of radiation from a Co$^{60}$ source. The solution was transferred to a beaker in a cool water bath and stirred. An additional 10.1 parts of the mercapto halopropanol were added and the solution was irradiated for 10 hours with an ultraviolet ray lamp. The resulting product was the diadduct of the diallyoxyethane.

Run 2:

A solution of 0.1 mol 1,4-diallyloxy-butene-2 and 0.3 mole of 1-mercapto-3-chloro-propanol-2 in 100 ml. isopropanol was subjected to 3.4 megarads of radiation from a Co$^{60}$ source and subsequently exposed to ultraviolet light for 8 hours. Unreacted ingredients were removed by flash distillation. The sulfur content of the reaction product corresponded to a diadduct.

Run 3:

When diallyl ether is employed as a reactant the end product obtained can be either a diadduct of the mercapto halopropanol or a mixture of monoadduct, diadduct and a cyclic ether adduct.

Run 4:

To a beaker containing 0.6 mole of 1-mercapto-3-chloro-2-propanol which was irradiated with ultraviolet light was added 0.2 mol of diallyl ether dropwise over a period of about 20 minutes. The mixture was irradiated for about 1.3 hours after adding the diallyether. Stirring was continuous during the entire process. The crude product was flash distilled at 80° and .15 mm. leaving an 88% yield of the diadduct. To obtain good yields of the diadduct, the mercapto-halopropanol should always be present, preferably in fairly large excess as compared to the diallyl ether.

Run 5:

To one mole of diallyl ether, irradiated with ultraviolet light, one mole of 1-mercapto-3-chloro-2-propanol was added dropwise over a period of two hours. The crude product was flash distilled at 80° C and 0.15 mm. The distillate consisted of CH$_2$=CHCH$_2$O(CH$_2$)$_3$SCH$_2$CH$_2$OHCH$_2$Cl and

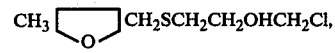

while the distillation residue was mainly diadduct. When dimethallyl ether is substituted for diallyl ether, the cyclic ether formed by this procedure has the structure,

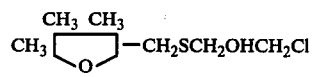

To obtain the best yields of the cycloether adduct, the diallylether or its β-substituted derivatives should be present in relatively large excess as compared to the mercapto halopropanol.

Run 6:

A mixture of 2,5-dihydrofuran and 1-mercapto-3-chloro-2-propanol was irradiated with ultraviolet light for about 18 hours. The product obtained had the structure

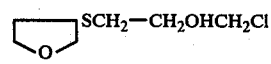

Run 7:

Reaction of one mole of allyl glycidyl ether with 2 moles of chloromercaptopropanol forms essentially 100% of a product with the structure ClCH$_2$CHOHCH$_2$S—(CH$_2$)$_3$OCH$_2$-
CHOHCH$_2$SCH$_2$CHOHCH$_2$Cl .

This reaction was carried out under ultraviolet light irradiation for 3½ hours. In another run 0.05 mole of

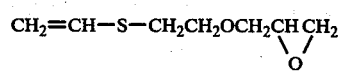

was reacted with 0.1 mole of chloromercaptopropanol at autogenous temperature for three days. Analysis showed that 88% of the epoxy groups were reacted and only a trace of unsaturation remained. The compound formed had the structure ClCH$_2$CHOHCH$_2$SC$_2$H$_4$SC$_2$H$_4$OCH$_2$-
CHOHCH$_2$SCH$_2$CHOHCH$_2$Cl .

A typical representative of unsaturated esters which react with mercapto halopropanol is allyl acetate. A mixture of 85% purity allyl acetate and 1-mercapto-3-chloro-2-propanol in a mole ratio of 1 to 2 was allowed to stand overnight. The mixture was fractionally distilled and a fraction boiling at 126°–127° C and 0.1 mm. pressure was obtained in an 92% yield. This fraction had a refractive index at 25° C of 1.4995.

When purified allyl acetate as a reactant was substituted for the 85% material and the mixture was irradiated with ultraviolet light for 3½ hours, the yield of purified material, obtained as described above, was 82%. This fraction had a refractive index of 1.4988.

Other unsaturated esters which were reacted in a mole ratio of 2 MCP to 1 of ester to form adducts with 1-mercapto-3-chloro-2-propanol are diallyl isophthalate (at 100% reacted under 3 megarads radiation), diallyl maleate, diallyl adipate, di(4-cyclohexenyl)methyl succinate (10 hours exposure to ultraviolet light, 72% yield of brown liquid), diethylene glycol undecylenate (about 10 hours U.V. radiation. 59.6% yield of brown liquid), triallyl trimesate,

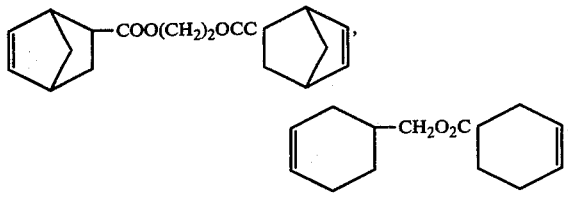

EXAMPLE 18

In this example, representative compounds having one or more aliphatically unsaturated hydrocarbon groups attached to a nitrogen atom are employed as one reactant with a mercapto halopropanol. In all instances, the reactions were catalyzed by ultraviolet light. Listed below are the compounds reacted with 1-mercapto-3-chloro-2-propanol, the mol ratios of reactants, the reaction period and the yields obtained.

TABLE VI

| Run No. | Olefin | Mol Ratio MCP/olefin | U.V. Hrs. | Percent Yield |
|---|---|---|---|---|
| 1 | N,N,N',N' tetraallyl-terephthalimide | 4:1 | (a) | — |
| 2 | N,N-diallyl acetamido | 2:1 | 5 | 5 (diadduct) |
| 3 | N,N-diallyl-formamide | 2:1 | | — |
| 4 | N,N-diallyl 3-butencoicacid-amide | 3:1 | (a) | — |
| 5 | N,N-diallyl undecylamido | 3:1 | (a) | — |
| 6 | N,N,N',N'-tetrallyl-adipamide | 4:1 | 10½ | — |
| 7 | N,N-diallyl benzamide | 2:1 | | — |
| 8 | N,N-diallyl 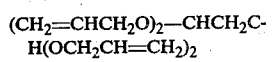 | 3:1 | (a) | — |
| 9 | N,N-diallyl benzenesulfon-amide | 2:1 | 3 | — |
| 10 | N-allyl succinimide | 2:1 | 2½ | 75 |
| 11 | N-allyl 1,2-dicarboxy-4-cyclohexeneimide | 2:1 | 7½ | 81 |
| 12 | Triallycyanurate | 4:1 | 12½ | 38 |

(a)3.5 megarads from a Co$^{60}$ source

N,N-Diallylamides and N,N-diallylsulfonamides in addition to forming the expected diadduct may form two monoadducts. In addition to the expected open chain monoadduct, a cyclic monoadduct of the type

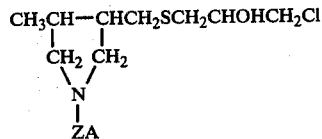

where Z is

or —SO$_2$— and A is the remaining residue of the carboxylic or sulfonic acid. In general, the cyclic adduct is formed in preference to the open chain adducts unless a large excess of mercaptan is used.

The double bond in the acid portion of unsaturated amides such as those derived from undecyl amide, 2,2,1-bicyclohept-5-ene-2-carboxylic amide, or 4-cyclohexenecarboxamide are also reactive.

Unsaturated Acetals

The tetrallyl acetal of allyl alcohol and 1,3-propane dialdehyde having the structure (CH$_2$=CHCH$_2$O)$_2$—CHCH$_2$CH(OCH$_2$CH=CH$_2$)$_2$ was reacted with 4.0 moles of 1-mercapto-3-chloro-2-propanol by using Co$^{60}$ as a free radical initiator. The product obtained from this reaction was a viscous brown liquid.

Other representative acetals which can be reacted to form adducts with the above defined mercaptohalopropanol include but are not limited to the allyl alcohol acetals of acetaldehyde, propionaldehyde, benzaldehyde, acrolein, methacrolein, 4-cyclohexenyl aldehyde, the aldehyde

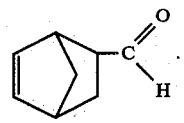

Addition may occur at the double bond of the allyloxy group, or addition can also take place at other sites of unsaturation such as those in acetals of acrolein and 4-cyclohexene aldehyde.

It is apparent from the above that the N-diallyl substituted mono or dicarboxylic acids can have 1 to 11 C atoms in the acid moiety, the N-allyl imide contain 4–8 C atoms in the acid moiety and the sulfonamides contain 6 C atoms in the sulfonic acid moiety.

We claim:
1. A compound of the formula R(SCH$_2$CH(OH)CH$_2$X)$_n$ in which X is chlorine or bromine, R is the residue of a triallyl cyanurate of the formula

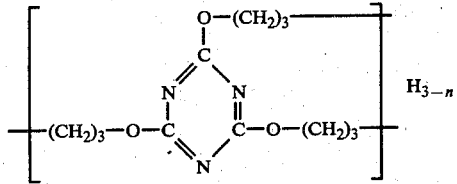

and n is 1 to 3.

2. A compound of claim 13 of the formula

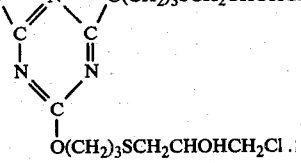

* * * * *

UNITED STATES PATENT AND TRADEMARK OFFICE
CERTIFICATE OF CORRECTION

PATENT NO. : 4,126,746

DATED : November 21, 1978

INVENTOR(S) : Richard S. Hickner and Corwin J. Bredeweg

It is certified that error appears in the above-identified patent and that said Letters Patent are hereby corrected as shown below:

Column 1, line 10, "halogne" should read --halogen--.

Column 1, line 15, "R—(—S—CH$_2$CHOHCHX)$_n$" should read
--R—(—S—CH$_2$CHOHCH$_2$X)$_n$--.

Column 1, line 20, "thiocthere" should read --thioether--.

Column 3, line 34, "he" should read "the".

Column 3, line 50, "172-3" should read --72-3--.

Column 4, line 52, "copolymes" should read --copolymers--.

Column 6, line 31, delete "%".

Column 6, line 32, delete "%".

Column 7, starting line 37, the product formed by Alpha pinene should read

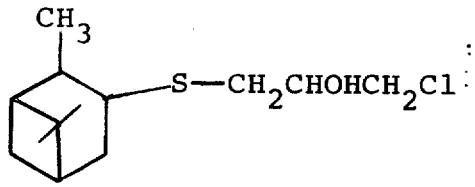

Column 8, line 29, "1,1,2-trifuoroethylene" should read --1,1,2-trifluoroethylene--.

Column 9, Table IV, Run No. 2, "12 diallyloxybenzene" should read --1,2 diallyloxybenzene--.

UNITED STATES PATENT AND TRADEMARK OFFICE
CERTIFICATE OF CORRECTION

PATENT NO. : 4,126,746

DATED : November 21, 1978

INVENTOR(S) : Richard S. Hickner and Corwin J. Bredeweg

It is certified that error appears in the above-identified patent and that said Letters Patent are hereby corrected as shown below:

Column 9, Table IV, Run No. 5, "2,2-bis(3-allyl-4-allyloxy phenyl)propano should read --2,2-bis(3-allyl-4-allyloxy phenyl) propane--.

Column 12, Table V, in the heading "RAtio" should read --Ratio--.

Column 13, lines 52 and 53, "diallyether" should read --diallylether--.

Column 15, Run No. 2, "5(diadduct)" should read --50 (diadduct)--.

Column 15, Run No. 12, "Triallycyanurate" should read --Triallylcyanurate--.

Column 15, Run No. 12, "12 1/2" should read --13 1/2--.

UNITED STATES PATENT AND TRADEMARK OFFICE
CERTIFICATE OF CORRECTION

PATENT NO. : 4,126,746

DATED : November 21, 1978

INVENTOR(S) : Richard S. Hickner and Corwin J. Bredeweg

It is certified that error appears in the above-identified patent and that said Letters Patent are hereby corrected as shown below:

Column 16, line 58, "13" should read --1--.

Signed and Sealed this

Twelfth Day of June 1979

[SEAL]

Attest:

RUTH C. MASON
*Attesting Officer*

DONALD W. BANNER
*Commissioner of Patents and Trademarks*